(12) United States Patent
Alam et al.

(10) Patent No.: US 9,376,432 B2
(45) Date of Patent: *Jun. 28, 2016

(54) USE OF VEGFR-3 INHIBITORS FOR TREATING HEPATOCELLULAR CARCINOMA

(71) Applicant: Sanofi, Paris (FR)

(72) Inventors: Antoine Alam, Paris (FR); Isabelle Blanc, Paris (FR)

(73) Assignee: SANOFI, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/414,209

(22) PCT Filed: Jul. 16, 2013

(86) PCT No.: PCT/EP2013/065029
§ 371 (c)(1),
(2) Date: Jan. 12, 2015

(87) PCT Pub. No.: WO2014/012942
PCT Pub. Date: Jan. 23, 2014

(65) Prior Publication Data
US 2015/0183780 A1    Jul. 2, 2015

Related U.S. Application Data

(60) Provisional application No. 61/672,489, filed on Jul. 17, 2012.

(30) Foreign Application Priority Data

Jul. 17, 2012    (EP) .................................... 12305866

(51) Int. Cl.
C07D 471/04    (2006.01)
A61K 31/4375   (2006.01)
A61P 35/00     (2006.01)

(52) U.S. Cl.
CPC .......... *C07D 471/04* (2013.01); *A61K 31/4375* (2013.01)

(58) Field of Classification Search
CPC ... C07D 471/04; A61K 31/4375; A61P 35/00
USPC ......................................... 514/300; 546/122
See application file for complete search history.

(56) References Cited

U.S. PATENT DOCUMENTS 8,470,847 B2 *  6/2013  Alam et al. ................. 514/300
9,126,972 B2 *  9/2015  Braun et al. ......... C07D 401/04

(Continued)

FOREIGN PATENT DOCUMENTS

WO    WO 98/39332 A1    9/1998
WO    WO 2009/007535 A2    1/2009

(Continued)

OTHER PUBLICATIONS

Alam; Molecular Cancer Therapeutics, 2012, 11, 1637-1649.*

(Continued)

*Primary Examiner* — Janet L Andres
*Assistant Examiner* — Daniel Carcanague
(74) *Attorney, Agent, or Firm* — Lathrop & Gage LLP; James H. Velema

(57) ABSTRACT

This invention is related to the use of inhibitors of vascular endothelial growth factor receptor 3 for treating hepatocellular carcinoma.

5 Claims, 2 Drawing Sheets

Mean +/- SEM ; *:p< 0.05; : p<0.01 and * p<0.001, ANOVA test versus control group. Statistical analysis on the total raw data (tumor+ liver lobe weight)

(56) References Cited

U.S. PATENT DOCUMENTS

| | | | |
|---|---|---|---|
| 2010/0144757 A1* | 6/2010 | Alam et al. | 514/255.05 |
| 2011/0251194 A1* | 10/2011 | Bernhart et al. | 514/234.5 |
| 2013/0005724 A1* | 1/2013 | Lassalle et al. | 514/234.5 |
| 2014/0094488 A1* | 4/2014 | Braun et al. | 514/300 |

FOREIGN PATENT DOCUMENTS

| | | | |
|---|---|---|---|
| WO | WO 2010/004198 | * | 1/2010 |
| WO | WO 2010/073078 A2 | | 7/2010 |
| WO | WO 2011/061458 | * | 5/2011 |
| WO | WO 2012/159959 A1 | | 11/2012 |

OTHER PUBLICATIONS

Hopfner; World Journal of Gastroenterology, 2008, 14, 1-14.*
International Search Report for PCT/EP2013/065029 completed Aug. 5, 2013.
Ivy, et al., "An overview of small-molecule inhibitors of VEGFR signaling" Nature Reviews Clinical Oncology, 6, 569-579 (2009).

* cited by examiner

Mean +/- SEM ; *:p< 0.05; : p<0.01 and * p<0.001, ANOVA test versus control group. Statistical analysis on the total raw data (tumor+ liver lobe weight)

USE OF VEGFR-3 INHIBITORS FOR TREATING HEPATOCELLULAR CARCINOMA

RELATED APPLICATIONS

This application is a 371 filing of International Application No. PCT/EP2013/065029, filed Jul. 16, 2013, which claims priority to U.S. Provisional Patent Application No. 61/672,489, filed Jul. 17, 2012 and European Patent Application No. 12305866.1, filed Jul. 17, 2012, the contents of each of which are incorporated herein by reference in their entirety.

This invention is related to the use of inhibitors of vascular endothelial growth factor receptor 3 for treating hepatocellular carcinoma (HCC).

Hepatocellular carcinoma (HCC) is the fifth most common solid tumor worldwide and its incidence has been steadily increasing over the 25 years (Thomas et al. Hepatocellular carcinoma: consensus recommendations of the National Cancer Institute Clinical Trials Planning Meeting. *J Clin Oncol.* 2010; 28(25):3994-4005). HCC is a deadly disease with worldwide annual death of more than 600,000. The unmet need is extremely high, especially in Asia-Pacific region (Kudo et al. Asian consensus workshop report: expert consensus guideline for the management of intermediate and advanced hepatocellular carcinoma in Asia. *Oncology* 2011. 81:158-64). In China, about 400,000 new cases are diagnosed every year. The majority of them are diagnosed at advanced stages with limited options for treatment. Only 20% are eligible for surgery with very high recurrence rate. Until now, only Sorafenib, a multi-kinase inhibitor, is approved for HCC therapy. It gives rise to 2-3 months OS (overall survival)>placebo and less than 5% of patients are eligible due to its highly associated toxicity (Song et al. A single center experience of sorafenib in advanced hepatocellular carcinoma patients: evaluation of prognostic factors. *Eur. J. Gastroenterol Hepatol.* 2011 (12):1233-8).

Vascular endothelial growth factor receptor 3 (VEGFR-3) is a tyrosine kinase receptor which recognizes two ligands VEGFC and VEGFD. Tumor-associated lymphangiogenesis in HCC correlates with poor prognosis and patients survival (Thelen et al. Tumor-Associated Lymphangiogenesis Correlates with Prognosis after Resection of Human Hepatocellular Carcinoma. *Ann. Surg. Oncol.* (2009) 16:1222-1230; Thelen et al. Tumor-associated angiogenesis and lymphangiogenesis correlate with progression of intrahepatic cholangiocarcinoma. *Am. J. Gastroenterol.* 105(5):1123-32, 2010). In contrast to normal liver specimens, most HCC tissue specimens revealed a strong immunoreactivity for VEGF-D (Thelen et al. VEGF-D promotes tumor growth and lymphatic spread in a mouse model of hepatocellular carcinoma *Int. J. Cancer:* 122, 2471-2481 2008). In addition, clinical trial data suggest high level of VEGF-C at baseline was significantly associated with prolonged OS following sunitinib (a pan-VEGFR inhibitor) treatment (Harmon et al. Mechanism-related circulating proteins as biomarkers for clinical outcome in patients with unresectable hepatocellular carcinoma receiving sunitinib *J. Transl. Med.* 2011 Jul. 25; 9:120). Moreover, expression of VEGFR-3 has been described to be upregulated in >75% of Hepatitis B X antigen (HBxAg) positive HCC nodules and was inversely related to HCC patient survival (Lian et al. Hepatitis B x Antigen Up-regulates Vascular Endothelial Growth Factor Receptor 3 in Hepatocarcinogenesis. *HEPATOLOGY*, Vol. 45, No. 6, 2007). Further, macrophages infiltration which may express VEGFR-3, are associated with intrahepatic metastasis, tumor recurrence, and poor patient survival. (Lin et al. Macrophage activation increases the invasive properties of hepatoma cells by destabilization of the adherens junction *FEBS Letters* 580 (2006) 3042-3050; Zhu et al. High expression of macrophage colony-stimulating factor in peritumoral liver tissue is associated with poor survival after curative resection of hepatocellular carcinoma. *J. Clin. Oncol.* 2008 Jun. 1; 26(16):2707-16; Ju et al. Peritumoral activated hepatic stellate cells predict poor clinical outcome in hepatocellular carcinoma after curative resection. *Am. J. Clin Pathol.* 2009 April; 131(4):498-510). However, until now, there is no specific VEGFR-3 inhibitor that has been reported in clinical phases for treating HCC.

International Application No. PCT/EP2012/059145 (the '145 application), filed May 16, 2012, discloses a compound of formula (I), wherein R is a methoxy or hydroxyl group, as VEGFR-3 inhibitors. It is now found that the compound of formula (I) is also useful for treating HCC.

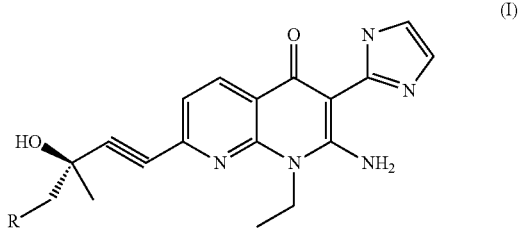

The present invention is related to a method for treating hepatocellular carcinoma comprising administering to a patient in need thereof a pharmaceutically effective amount of a compound of formula (I),

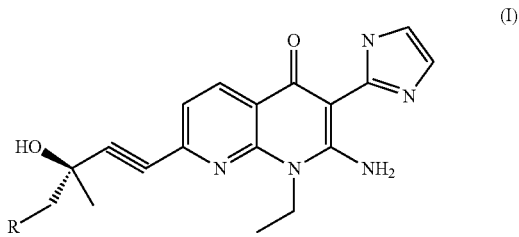

wherein R is a methoxy or hydroxyl group,
or a pharmaceutically acceptable salt thereof.

The present invention is also directed to a compound of formula (I) above, or a pharmaceutically acceptable salt thereof, for use in treating hepatocellular carcinoma.

The present invention is also directed to the use of a compound of formula (I) above, or a pharmaceutically acceptable salt thereof, for the preparation of a drug for use in the treatment of hepatocellular carcinoma.

The above and other aspects, features, and advantages of the present invention will be better understood from the following detailed description taken in conjunction with the accompanying drawings, all of which are given by way of illustration only, and are not limitative of the present invention.

Figure 1:
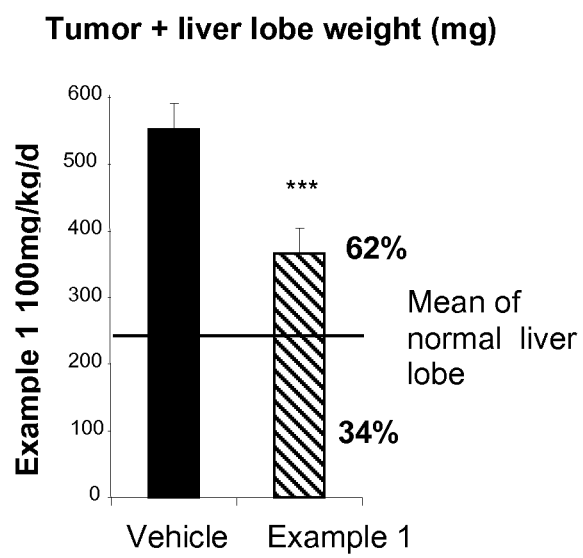
FIG. 1 shows the results of in vivo evaluation of the compound of Example 1 in murine hepatocarcinoma xenograft model.

As used above, and throughout the description of the invention, the following terms, unless otherwise indicated, shall be understood to have the following meanings:

"Compound of the invention" means the compound of formula (I) or a pharmaceutically acceptable salt thereof.

"Hepatocellular carcinoma" is one type of liver cancer arising from the liver cells. Liver damage, manifested by cirrhosis (scarring), is a primary risk factor for liver cancer. HCC, however, also includes solid liver carcinoma in the absence of liver cirrhosis.

"Patient" includes both human and other mammals.

"Pharmaceutically acceptable salts" refers to the relatively non-toxic, inorganic and organic acid addition salts, and base addition salts of the compound of formula I. These salts can be prepared in situ during the final isolation and purification of the compound of formula I. See, for example S. M. Berge, et al., "Pharmaceutical Salts," J. Pharm. Sci., 66, 1-19 (1977).

"Pharmaceutically effective amount" means an amount of a compound or composition according to the present invention effective in producing the desired therapeutic effect.

"Treating" or "treatment" means to alleviate symptoms, eliminate the causation of the symptoms either on a temporary or permanent basis, or to slow the appearance of symptoms of the named disorder or condition.

One particular embodiment of the invention is related to a method for treating hepatocellular carcinoma comprising administering to a patient in need thereof a pharmaceutically effective amount of 2-amino-1-ethyl-7-((3R)-3-hydroxy-4-methoxy-3-methyl-but-1-ynyl)-3-(1H-imidazol-2-yl)-1H-[1,8]-naphthyridin-4-one, or a pharmaceutically acceptable salt thereof.

Another embodiment of the invention is related to the compound 2-amino-1-ethyl-7-((3R)-3-hydroxy-4-methoxy-3-methyl-but-1-ynyl)-3-(1H-imidazol-2-yl)-1H-[1,8]-naphthyridin-4-one, or a pharmaceutically acceptable salt thereof, for use in treating hepatocellular carcinoma.

One particular embodiment of the invention is related to a method for treating hepatocellular carcinoma comprising administering to a patient in need thereof a pharmaceutically effective amount of 2-amino-1-ethyl-7-((3R)-3-hydroxy-4-methoxy-3-methyl-but-1-ynyl)-3-(1H-imidazol-2-yl)-1H-[1,8]-naphthyridin-4-one.

Another embodiment of the invention is related to the compound 2-amino-1-ethyl-7-((3R)-3-hydroxy-4-methoxy-3-methyl-but-1-ynyl)-3-(1H-imidazol-2-yl)-1H-[1,8]-naphthyridin-4-one for use in treating hepatocellular carcinoma.

Another particular embodiment of the invention is related to a compound of formula (I), wherein R is a methoxy or hydroxyl group, or a pharmaceutically acceptable salt thereof, for use in the preparation of a medicament for treating hepatocellular carcinoma.

Another particular embodiment of the invention is related to 2-amino-1-ethyl-7-((3R)-3-hydroxy-4-methoxy-3-methyl-but-1-ynyl)-3-(1H-imidazol-2-yl)-1H-[1,8]-naphthyridin-4-one, or a pharmaceutically acceptable salt thereof, for use in the preparation of a medicament for treating hepatocellular carcinoma.

Another particular embodiment of the invention is related to 2-amino-1-ethyl-7-((3R)-3-hydroxy-4-methoxy-3-methyl-but-1-ynyl)-3-(1H-imidazol-2-yl)-1H-[1,8]-naphthyridin-4-one for use in the preparation of a medicament for treating hepatocellular carcinoma.

A particular aspect of the invention provides for a compound of the present invention to be administered in the form of a pharmaceutical composition. A pharmaceutical composition, according to the present invention, comprises a compound of the present invention and a pharmaceutically acceptable carrier.

In practice, the compound of the invention may be administered to humans and other animals by oral or intravenous administration, in unit administration form, as a mixture with conventional pharmaceutical excipients.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion.

Pharmaceutical compositions of the present invention suitable for intravenous administration may be formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorption, metabolism and/or excretion and other factors.

The total daily dose of the compound of the invention administered to a patient in single or divided doses may be in amounts, for example, of from about 0.001 to about 100 mg/kg body weight daily and particularly 0.01 to 10 mg/kg/day. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The present invention may be better understood by reference to the following non-limiting examples, which is exemplary of the invention. They should in no way be construed, however, as limiting the broad scope of the invention.

EXAMPLE 1

2-Amino-1-ethyl-7-((3R)-3-hydroxy-4-methoxy-3-methyl-but-1-ynyl)-3-(1H-imidazol-2-yl)-1H-[1,8]-naphthyridin-4-one

Step 1: 6-Chloro-2-ethylamino-nicotinic acid

A solution of 18.0 g (84.4 mmol) of 2,6-dichloronicotinic acid in 180 ml of a solution of ethylamine (70% in water) was stirred at ambient temperature for 72 hours. The excess amine was then evaporated off under reduced pressure, and an aqueous solution of acetic acid at 10% was added until the product precipitates. The beige solid was spin-filter-dried, rinsed with cold water and dried in an oven. 10.5 g of the expected product were obtained.
Melting point=158-160° C.
Yield=62%.

Step 2: 6-Chloro-2-ethylamino-nicotinoyl fluoride 2 ml (24.8 mmol) of pyridine and 4.2 ml (49.8 mmol) of 2,4,6-trifluorotriazine were added to a suspension of 5.0 g (24.8 mmol) of 6-chloro-2-ethylamino-nicotinic acid in 125 ml of dichloromethane. The mixture was stirred for 3 hours at ambient temperature and then filtered. The solid was rinsed with 50 ml of dichloromethane and the filtrate was washed twice with 60 ml of ice-cold water. The organic phase was dried over $Na_2SO_4$ and the solvent was evaporated off under reduced pressure. 5.01 g of product were obtained in the form of an orange oil which was used without further purification.
Yield=99%.

Step 3: 1-(2-Trimethylsilanyl-ethoxymethyl)-1H-imidazole-2-carbaldehyde

An oily suspension of 20.8 g sodium hydride in mineral oil (50%, 0.52 mol) was washed mineral oil free by stirring with hexane 3-times and suspended in 400 ml DMF. Under stirring at ambient temperature 50.0 g (0.520 mol) imidazole-2-carbaldehyde was added to the suspension. After 1.5 h, 101 ml (0.572 mol) 2-(trimethylsilanyl)ethoxymethyl chloride was added and the reaction was stirred a further hour. Then excess water was added to the suspension and the reaction mixture was extracted three times with ethyl acetate. The organic phase was dried over $Na_2SO_4$ and the solvent was evaporated off under reduced pressure. The raw material was then purified by column chromatography (DCM) to yield 85.0 g (0.376 mol) of the SEM-protected imidazole-2-carbaldehyde.
Yield=72%
MH+=227.1 ($C_{10}H_{18}N_2O_2Si$, Mr=226.35)
1H NMR (DMSO-d6, 500 MHz): δ 9.83 (s, 1H); 7.86 (s, 1H); 7.39 (s, 1H); 5.75 (s, 2H); 3.58 (t, 2H); 0.95 (t, 2H); 0.02 (s, 9H)

Step 4: [1-(2-Trimethylsilanyl-ethoxymethyl)-1H-imidazol-2-yl]-acetonitrile 1.73 g (8.84 mmol) tosylmethylisocyanide were solved in 10 ml DME and cooled down to −60° C. At this temperature first 1.98 g potassium tert-butoxide was added then slowly a solution of 2.00 g (8.84 mmol) 1-(2-trimethylsilanyl-ethoxymethyl)-1H-imidazole-2-carbaldehyde in 5 ml DME. After 2 hours stirring at −60° C. the reaction was allowed to reach 0° C. and 5 ml methanol (123.60 mmol) was added to the solution. The reaction was stirred for further 24 hours at ambient temperature and for 2 hours at 40° C. Excess water was added and the solution was extracted 3 times with dichloromethane. The organic phase was dried over $Na_2SO_4$, after evaporation of the solvent under reduced pressure the raw material was purified by reverse phase column chromatography (water 0.1% TFA/acetonitrile=80/20 to yield 0.87 g (0.367 mol) of the SEM-protected imidazole-acetonitrile.
Yield=41%
MH+=238.1 ($C_{11}H_{19}N_3OSi$, Mr=237,38)
1H NMR (DMSO-d6, 500 MHz): δ 7.66 (s, 1H); 7.39 (s, 1H); 5.53 (s, 2H); 4.52 (s, 2H); 3.55 (t, 2H); 0.92 (t, 2H); 0.02 (s, 9H)

Step 5: 3-(6-Chloro-2-ethylamino-pyridin-3-yl)-3-hydroxy-2-[1-(2-(trimethylsilanyl-ethoxymethyl)-1H-imidazol-2-yl]-acrylonitrile 0.283 g (2.53 mmol) of potassium tert-butylate was added, in small amounts, to a 0° C. solution of 0.600 g (2.53 mmol) [1-(2-trimethylsilanyl-ethoxymethyl)-1H-imidazol-2-yl]-acetonitrile in 10 ml of anhydrous THF. The mixture was stirred for 45 minutes at ambient temperature, and was then cooled again to 0° C. A solution of 0.512 g (2.53 mmol) 6-chloro-2-ethylamino-nicotinoyl fluoride in 10 ml of THF was then added and the medium was stirred at ambient temperature overnight, again cooled down to 0° C. and a second equivalent of potassium tert-butylate (0.283 g, 2.53 mmol) was added. After 2 h stirring at ambient temperature 50 ml saturated ammonium chloride aqueous solution was added, the pH was adjusted to 7 with 2N HCl then extracted three times with ethyl acetate. The combined organic phases were dried over $MgSO_4$ and the solvents were evaporated under reduced pressure. The raw material was further purified by column chromatography (DCM/Methanol=90:10) yielding 418 mg (yield=38%) of the title compound.
MH+=421 ($C_{19}H_{26}ClN_5O_2Si$, Mr=419,99)
1H NMR (DMSO-d6, 500 MHz): δ 13.35 (s, 1H); 7.70 (d, 1H); 7.46 (s, 1H); 7.23 (s, 1H); 7.08 (t, 1H); 6.58 (d, 1H); 5.59 (s, 2H); 3.58 (t, 2H); 3.34 (dq, 2H); 1.13 (t, 3H); −0.03 (3s, 9H).

Step 6: 2-Amino-7-chloro-1-ethyl-3-[1-(2-trimethylsilanyl-ethoxymethyl)-1H-imidazol-2-yl]-1H-[1,8]naphthyridin-4-one 0.112 g (1 mmol) of potassium tert-butylate was added, in small amounts, to a 0° C. cold solution of 418 mg (1 mmol) of the intermediate prepared under 1.53-(6-chloro-2-ethylamino-pyridin-3-yl)-3-hydroxy-2-[1-(2-(trimethylsilanyl-ethoxymethyl)-1H-imidazol-2-yl]-acrylonitrile in 5 ml of anhydrous THF. The mixture was stirred for 48 h at ambient temperature after which 50 ml of saturated ammonium chloride aqueous solution was added, the pH was adjusted to 7 with 2N HCl and the reaction mixture was extracted three times with ethyl acetate. The combined organic phases were dried over $MgSO_4$ and the solvents were evaporated under reduced pressure yielding 400 mg of the title compound.
Yield=38%
MH+=421 ($C_{19}H_{26}ClN_5O_2Si$, Mr=419,99)
1H NMR (DMSO-d6, 500 MHz): δ 8.50 (d, 1H); 8.03 (s, 1H); 7.98 (s, 1H); 7.78 (s, 2H); 7.60 (s, 1H); 5.49 (s, 2H); 4.58 (q, 2H); 3.57 (t, 2H); 1.42 (t, 3H); 0.85 (t, 2H); −0.03 (3s, 9H).

Step 7: (±)-2-Methyl-but-3-yne-1,2-diol

A commercially available 0.5 M solution of ethynylmagnesium chloride in tetrahydrofuran was diluted with 200 ml of tetrahydrofuran and cooled to 0° C. Then a solution of hydroxyacetone in 200 ml of tetrahydrofuran is added and the mixture was stirred at ambient temperature for 3 hours. The reaction mixture was cooled and an aqueous solution of $NH_4Cl$ was added. The mixture was extracted 3 times with ethyl acetate and the organic phases were combined, dried over sodium sulphate, filtered, and concentrated under vacuum (approximately 200 mbar). Finally, 20 g of expected product were obtained in the form of a brown oil, which was used without subsequent purification (quantitative crude yield) in the racemic form or could be separated in the pure enantiomers by preparative HPLC on chiral HPLC columns. In order to obtain the optically pure enantiomers, the corresponding racemic mixture was subjected to preparative chromatography on a chiral stationary phase (Chiralpak AD-H column, 250×21 mm, 5 mm) using, as mobile phase: either $CO_2$/2-propanol (70%/30%) with a flow rate of 60 ml/min at a pressure of 100 bar or an isohexane/ethanol (70/30) mixture with 0.3% of TFA and a flow rate of 120 ml/min.

After elution and evaporation, each enantiomer was isolated, and the chemical purity and enantiomeric purity of each were determined by analytical methods known to those skilled in the art.

Step 8: 2-Amino-1-ethyl-7-((3R)-3-hydroxy-4-methoxy-3-methyl-but-1-ynyl)-3-[1-(2-trimethylsilanyl-ethoxymethyl)-1H-imidazol-2-yl]-1H-[1,8]naphthyridin-4-one In an argon filled microwave reaction flask 500 mg (1.2 mmol) 2-amino-7-chloro-1-ethyl-3-[1-(2-trimethylsilanyl-ethoxymethyl)-1H-imidazol-2-yl]-1H-[1,8]naphthyridin-4-one, 204 mg (1.8 mmol) (3R)-1-methoxy-2-methyl-but-3-yn-2-ol, 84 mg (0.120 mmol) bis(triphenylphosphine)palladium (II) dichloride, 30 mg (0.16 mmol) copper (I) iodide, 2 ml DMF (degassed), 2 ml triethylamine (degassed) were given and irradiated in the microwave in such a way that the reaction mixture was kept at 120° C. for 24 h. The solvents were evaporated and the solid resuspended in 3 ml DMF and filtrated. The filtrate was then purified by HPLC yielding 430 mg (0.702 mmol) of the TFA salt of the title compound.

Yield=59%.
MH+=498.2 ($C_{25}H_{35}N_5O_4Si$, Mr=497,67).
1H NMR (DMSO-d6, 500 MHz): δ 8.39 (d, 1H); 7.95 (s, 1H); 7.88 (s, 1H); 7.60 (s, 2H); 7.48 (d, 1H); 5.25 (s, 2H); 4.50 (broad signal, 2H); 3.52-3.40 (broad signal, water peak+4H); 1.48 (s, 3H); 1.25 (t, 3H); −0.12 (3s, 9H).

Step 9: 2-Amino-1-ethyl-7-((3R)-3-hydroxy-4-methoxy-3-methyl-but-1-ynyl)-3-(1H-imidazol-2-yl)-1H-[1,8]naphthyridin-4-one 240 mg (0.4 mmol) SEM protected naphthyridinone 1.8 was solved at 0° C. in 1.2 ml TFA and 1.2 ml DCM. The solution was kept at 3-5° C. overnight until analytical HPLC showed complete deprotection of the naphthyridinone. The solution is neutralized by adding an excess of aqueous $NaHCO_3$ solution. The mixture was then extracted three times with ethyl acetate. The combined organic phases were dried over $MgSO_4$ and the solvents were evaporated off under reduced pressure. The so gained raw material was purified on silica gel (DCM:MeOH=4:1) yielding 143 mg (quantitative yield) of the unprotected title compound.

MH+=368.2 ($C_{19}H_{21}N_5O_3$, Mr=367,41)
1H NMR (DMSO-d6, 500 MHz): δ 13.15 (s, 1H); 11.55 (b s, 1H); 8.59 (d, 1H); 8.10 (b s, 1H); 7.47 (d, 1H); 7.25 (s, 1H); 7.02 (s, 1H); 5.85 (s, 1H); 4.58 (broad signal, 2H); 3.51-3.370 (broad signal, water peak+4H); 1.48 (s, 3H); 1.25 (t, 3H)
Rt (analytical HPLC): 4.806 min

EXAMPLE 2

2-Amino-7-((3R)3,4-dihydroxy-3-methyl-but-1-ynyl)-1-ethyl-3-(1H-imidazol-2-yl)-1,8-naphthyridin-4(1H)-one

Step 1: 2-Amino-1-ethyl-7-(3,4-dihydroxy-3-methyl-but-1-ynyl)-1-ethyl-3-[1-(2-trimethylsilanyl-ethoxymethyl)-1H-imidazol-2-yl]-1,8-naphthyridin-4(1H)-one Following the procedure according to step 8 of Example 1, using the intermediate described under step 6 of Example 1 (2-amino-7-chloro-1-ethyl-3-[1-(2-trimethylsilanyl-ethoxymethyl)-1H-imidazol-2-yl-1,8-naphthyridin-4(1H)-one) and step 7 of Example 1 ((±)-2-methyl-but-3-yne-1,2-diol), the titled compound was obtained.

MH+=354.16 ($C_{18}H_{19}N_5O_3$, Mr=353,38)
Rt (analytical HPLC): 4.48 min

Step 2: 2-Amino-1-ethyl-7-((3R)3,4-dihydroxy-3-methyl-but-1-ynyl)-1-ethyl 3-[1-(2-trimethylsilanyl-ethoxymethyl)-1H-imidazol-2-yl]-1,8-naphthyridin-4(1H)-one The racemic compound obtained at step 1 was subjected to a preparative Chiral SFC purification, using a methods, Berger prep SFC, UV detection at 230 nm, stationary phase Chiralpak IC 20×250 nm 5 μm, mobile phase 65%/35% CO2/(MeOH+à.5% isopropylamine), 50 ml/min, 100 bars) leading to the separation of the R and S enantiomers.

The chiral purity was controlled using Chiral SFC methods, Berger SFC, UV detection at 210 nm, stationary phase Chiralpak AD-H (250 mm×4.6) 5 μm, mobile phase 65/35% CO2/(isopropanol+0.5% isopropylamine), 2.4 ml/min, 100 bars. R enantiomer (Rt=6.9 min, enantiomeric purity=97.9%)

Step 3: 2-Amino-7-((3R)3,4-dihydroxy-3-methyl-but-1-ynyl)-1-ethyl-3-(1H-imidazol-2-yl)-1,8-naphthyridin-4(1H)-one Following the procedure according to step 9 of Example 1, the compound of Example 2 is isolated as a yellow powder.
MH+=354.16 ($C_{18}H_{19}N_5O_3$, Mr=353,38)
Rt=0.77 min
1H NMR (DMSO-d6, 400 MHz): δ 13.15 (s, 1H); 11.55 (bs, 1H); 8.55 (d, 1H, J=6.4 Hz); 8.10 (bs, 1H); 7.47 (d, 1H, J=6.4 Hz); 7.15 (s, 1H); 7.02 (s, 1H); 5.6 (s, 1H); 5.1 (t, 1H, J=6.4 Hz) 4.53 (bd, 2H); 3.49 (dd, 1H, J=6.4; 10.4 Hz); 3.41 (dd, 1H, J=6.4; 10.4 Hz) 1.48 (s, 3H); 1.27 (t, 3H, J=7.2 Hz).

The chiral purity was controlled using Chiral SFC methods, Berger SFC, UV detection at 230 nm, stationary phase Chiralpak AD-H (250 mm×4.6) 5 μm, mobile phase 60/40% CO2/(isopropanol+0.5% isopropylamine), 2.4 ml/min, 100 bars. R enantiomer (Rt=8.37 min, enantiomeric purity=99.2%)

Analytical Method LC/UV/MS Retention Time (Rt) Detection

Column: Merk Chromolith performance RP18e, 100×4.6 mm, 3.5 μm
Solvent A: $H_2O$/TFA (99.9/0.1)
Solvent B: ACN/TFA (99.9/0.1)
Flow rate: 2 ml/min
Gradient (A/B): 98/2 (0 min) to 0/100 (8 min) to 98/2 (10 min)
Detection: 254.16 nM
NMR
The 1H NMR spectra were obtained using NMR spectrometers Bruker 250, 300, 400, or 600 MHz in DMSO-d6, using the peak of DMSO-d5 as internal reference. The chemical shifts δ expressed in parts per million (ppm).

The signals observed are expressed as follows: s=singlet; d=doublet; t=triplet; q=quadruplet; m=multiplet or large singlet; br=broad; H=proton.

Melting Points

The melting point was measured with a Kofler bench.

Pharmacological Testing

I. In Vitro Evaluation of the Compound of Example 1

The '145 application discloses that the compounds of Examples 1 and 2 inhibits recombinant VEGFR-3 TK activity and autophosphorylation in HEK cells with an IC50 about 25 nM and 47 nM, respectively. In the same assays, the compound of Example 1 exhibited less activity on VEGFR-2 (90 nM-140 nM) and on VEGFR-1 (>1 µM). Using primary lymphatic cells we confirmed the high activity towards VEGFR-3, since it inhibits VEGFC- and VEGFD-induced proliferation with an IC50 about 10-15 nM. Moreover, we demonstrated that the compound of Example 1 is highly selective for VEGFR-3 compared to all other tested kinases (85 different kinases) and to 107 receptors, enzymes and ion channels.

II. In Vivo Evaluation of the Compound of Example 1 in Murine Hepatocarcinoma Xenograft Model.

The in vivo anti-tumor efficacy of the compound of Example 1 in HepG2 cell line orthotopic xenograft model was evaluated. The HepG2 cells were injected into liver of SCID mice (obtained from ATCC) and mice were randomized into 2 groups 14 days post cell injection: a control group treated with vehicle and the compound of Example 1-treated group. Treatment was performed once a day at 100 mg/kg in methyl cellulose tween as vehicle.

The tumor size was measured by weighting the left lobe with the tumor at day 28. The treatment by the compound of Example 1 significantly decreased the mean weight of the liver lobe bearing the tumor at Day 28 post cell injection by 34% (p=0.001, Student t-test). Normal liver lobe was also measured and deduced from the lobe of tumor bearing mice. In that case the compound of Example 1 reduced tumor weight by 62%. (See FIG. 1).

III. In Vivo Evaluation of the Compound of Example 1 on Chemical-Induced Hepatocarcinoma in Mice DEN (N-diethynitrosamine)-induced mouse model has been validated as a representative model for human HCC Wu et al. *J. Cancer Res. Clin. Oncol.* (2009) 135. 969-981; Chuang et al. *Carcinogenesis* (2000) 21; 331-335).

Tumor initiation was achieved by a single intra peritoneal injection of 10 mg/kg of N-diethylnitrosamine (DEN) in male C3H mice (Charles river laboratories France) at the age of 5 weeks.

Mice developed tumors in the liver from the 7th month post DEN administration but the incidence reached 100% at the 12th month. The compound of Example 1 was daily administrated P.O. (orally) after suspension in methyl cellulose tween, between the 10th and 12th month after DEN administration.

The body weight was evaluated each week during treatment and on the 12th months. Mice were killed by overdose of sodium pentobarbital, and livers were removed and weighted. The number of tumors per liver was counted and the tumor volume was measured with calipers. The tumor volume V was calculated using formula $V=0.52 \times a^2 \times b$, where "a" represents the smallest tumor diameter and "b" the largest tumor diameter.

Figure 2:
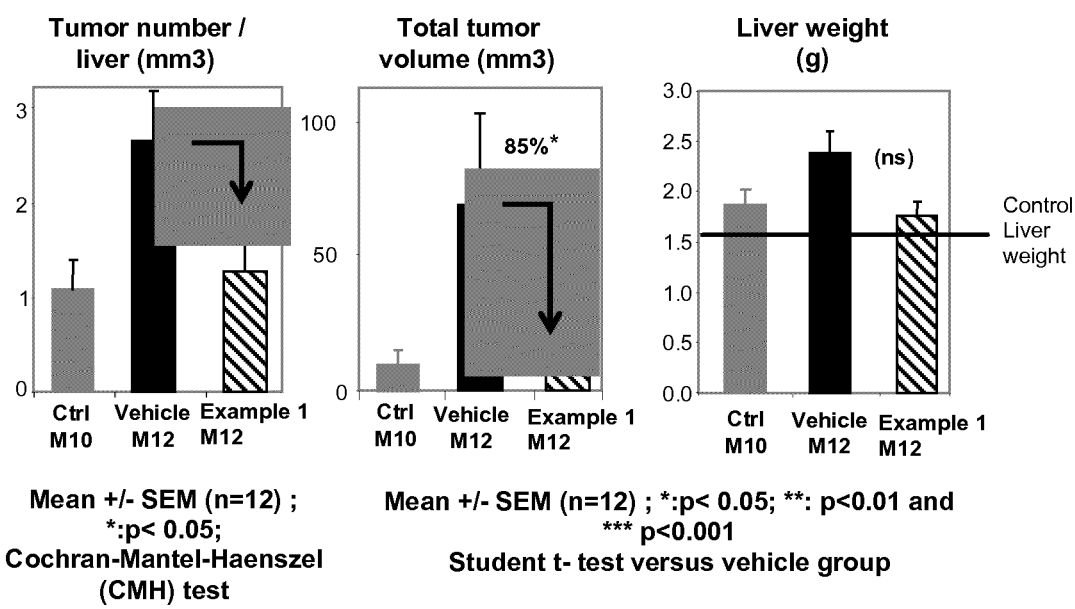
FIG. 2 shows the results of in vivo evaluation of the compound of Example 1 on chemical-induced hepatocarcinoma.

Late treatment with the compound of Example 1 prevented the formation of new loci and completely blocked tumor development when compared to the same parameters at the $10^{th}$ month. In comparison to the vehicle group, the compound of Example 1 reduced by 50% the number of tumors/liver and by 85% the total tumor volume. It also reduced and almost normalized the total liver weight. (see FIG. 2).

The invention claimed is:

1. A method of treating hepatocellular carcinoma comprising administering to a patient in need thereof a pharmaceutically effective amount of a compound of formula (I),

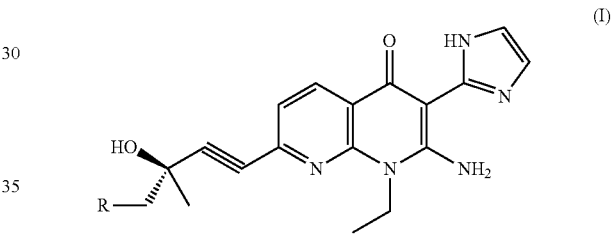

or a pharmaceutically acceptable salt thereof, wherein R is a methoxy or hydroxyl group.

2. The method according to claim 1, wherein R is a methoxy group.

3. The method according to claim 1, wherein R is a hydroxyl group.

4. The method according to any one of claims 1 and 2, wherein the compound of formula (I) is 2-amino-1-ethyl-7-((3R)-3-hydroxy-4-methoxy-3-methyl-but-1-ynyl)-3-(1H-imidazol-2-yl)-1H-[1,8]-naphthyridin-4-one.

5. The method according to any one of claims 1 and 3, wherein the compound of formula (I) is 2-amino-7-((3R)3,4-dihydroxy-3-methyl-but-1-ynyl)-1-ethyl-3-(1H-imidazol-2-yl)-1,8-naphthyridin-4(1H)-one.

* * * * *